United States Patent [19]

Devic et al.

[11] Patent Number: 5,352,826
[45] Date of Patent: Oct. 4, 1994

[54] SYNTHESIS OF ACYL CYANIDES IN AN ANHYDROUS REACTION MEDIUM

[75] Inventors: Michel Devic; Pierre Tellier, both of Saint Foy les Lyon, France

[73] Assignee: Atochem, Puteau, France

[21] Appl. No.: 35,879

[22] Filed: Mar. 23, 1993

Related U.S. Application Data

[63] Continuation of Ser. No. 832,620, Feb. 11, 1992, abandoned, which is a continuation of Ser. No. 525,730, May 21, 1990, abandoned.

[30] Foreign Application Priority Data

May 19, 1989 [FR] France ............................... 89 06563

[51] Int. Cl.$^5$ .................... C07C 255/18; C07C 253/14
[52] U.S. Cl. .................................................. 562/869
[58] Field of Search ........................................ 562/869

[56] References Cited

U.S. PATENT DOCUMENTS

| 4,113,773 | 9/1978 | Klenk et al. | 260/545 R |
| 4,143,068 | 3/1979 | Findeissen | 544/106 X |
| 4,209,461 | 6/1980 | Klenk et al. | 562/869 |
| 4,209,462 | 6/1980 | Photis | 562/869 |
| 4,555,370 | 11/1985 | Klauke et al. | 260/545 R |

FOREIGN PATENT DOCUMENTS 1520728 8/1979 United Kingdom .

*Primary Examiner*—Joseph Paul Brust
*Attorney, Agent, or Firm*—Burns, Doane, Swecker & Mathis

[57] ABSTRACT

The acyl cyanides (nitriles), notably benzoyl cyanide, are prepared by reacting an acid halide with an alkali metal cyanide, in an anhydrous solvent medium, in the presence of an alkylene oxide compound and a polar compound other than water, e.g., glycerol, ethylene glycol, formamide or a sugar derivative.

15 Claims, No Drawings

SYNTHESIS OF ACYL CYANIDES IN AN ANHYDROUS REACTION MEDIUM

CROSS-REFERENCE TO COMPANION APPLICATION

This application is a continuation of application Ser. No. 07/832,620, filed Feb. 11, 1992, now abandoned which is a continuation of application Ser. No. 07/525,730, filed May 21, 1990, now abandoned.

BACKGROUND OF THE INVENTION

1. Field of the Invention

The present invention relates to the synthesis of acyl cyanides and, more especially, to the synthesis of acyl cyanides by reacting acid halides with an alkali metal cyanide in an anhydrous reaction medium.

2. Description of the Prior Art

The acyl cyanides are known intermediates for a variety of organic syntheses, for example the production of herbicides.

FR 2,353,524 describes a synthesis of benzoyl cyanide $C_6H_5COCN$ by reacting benzoyl chloride with a molar excess of sodium cyanide in the presence of a nitrile of a carboxylic acid and copper cyanide.

FR 2,346,323 describes a similar, but much more general reaction, since it is applicable to an entire class of acyl cyanides, and entails reacting sodium cyanide with an excess of acid halide in the presence of copper or zinc cyanide.

The above processes present the disadvantage of requiring the presence of heavy metals and therefore mandate complicated treatments to avoid their presence in the reaction effluents.

*Tetrahedron Letters* (Pergamon Press) No. 26, pages 2275–2278 (1974) describes a process limited to the synthesis of benzoyl cyanide by reacting sodium cyanide with benzoyl chloride in solution in methylene chloride and in the presence of tetrabutylammonium bromide; the $C_6H_5COCN$ yield based on $C_6H_5COCl$ converted does not exceed 60%.

FR 2,364,894 describes the synthesis of $C_6H_5COCN$ by reacting $C_6H_5COCl$ with NaCN in a solvent in the presence of benzoic anhydride ($C_6H_5CO\text{-}O\text{-}CO\text{-}C_6H_5$) or of products which can generate benzoic anhydride under the reaction conditions.

The preferred amount of benzoic anhydride ranges from 0.03 to 0.1 mole per mole of benzoyl chloride. This presence of benzoic anhydride complicates the recovery of the benzoyl cyanide.

SUMMARY OF THE INVENTION

Accordingly, a major object of the present invention is the provision of an improved process for the preparation of the acyl cyanides, including benzoyl cyanide, but which does not form any benzoic anhydride byproduct.

Briefly, the present invention features the synthesis of acyl cyanides of the formula (I):

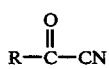
 (I)

in which R is either an alkyl radical having from 1 to 8 carbon atoms or a cycloalkyl radical having from 3 to 12 carbon atoms, or an aryl radical, or a heterocyclic radical which may be condensed with a benzene nucleus, all such radicals R being unsubstituted or substituted, comprising reacting an acid halide of the formula (II):

 (II)

in which R is as defined above and X is a halogen, with an alkali metal cyanide, (a) in anhydrous solvent medium, (b) in the presence of a compound containing alkylene oxide recurring units, and (c) in the further presence of a polar compound other than water.

DETAILED DESCRIPTION OF THE PREFERRED EMBODIMENTS OF THE INVENTION

More particularly according to the present invention, the subject reaction is carried out according to the reaction scheme:

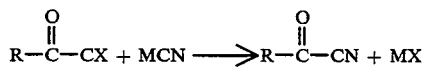

in which M is an alkali metal. Upon completion of the reaction, the alkali metal halide and the optional excess of alkali metal cyanide are removed by filtration and washing with solvent. The pure acyl cyanide is recovered by distillation of the filtered reaction mixture.

The acid halides employed as starting materials have the formula (II). In this formula, R is preferably a linear or branched chain alkyl radical having from 1 to 4 carbon atoms, or substituted such radicals.

Also preferably, R is a cycloalkyl radical having 5 or 6 carbons, or a substituted such radical.

Also preferably, R is a phenyl or naphthyl radical, or substituted such radicals.

Also preferably, R is a five- or six-membered heterocyclic radical, or a substituted such heterocycle.

In formula (II), X is advantageously chlorine or bromine.

The alkali metal, preferably sodium or potassium, cyanide is employed in stoichiometric amount or else in excess thereof, in a proportion of 1 to 2 moles per mole of acid halide; the preferred amount ranges from 1 to 1.25 moles per mole of acid halide.

The acid halide is generally added a little at a time to the reaction mixture. It is added either pure or diluted with the reaction solvent. The addition time period may range from a few minutes to several hours.

The preferred period of time is approximately 0.5 hours.

The reaction is carried out in the presence of a solvent, in sufficient amount to permit good stirring of the solid and liquid reactants.

Any solvent which does not react with the acid halide or with the alkali metal cyanide under the reaction conditions can be employed. Solvents of very low polarity are the preferred.

Exemplary of such solvents which are suitable for the reaction, the following are particularly representative:

(i) aromatic hydrocarbons, such as benzene, toluene, xylene, and the like, and halogenated aromatic hydrocarbons, such as chlorobenzene, dichlorobenzene, and the like;

(ii) aliphatic hydrocarbons, such as cyclohexane, ligroin, and the like;

(iii) halogenated aliphatic hydrocarbons, such as trichloroethylene, tetrachloroethane, and the like.

The preferred solvents for the reaction are toluene and xylene.

The amount of solvent may vary over wide limits. From 200 to 500 ml per mole of acid halide is typically sufficient.

It is also within the scope of the invention to use a larger amount of solvent, but this would require distilling a larger amount to recover the acyl cyanide.

The reaction can be carried out at temperatures ranging from 60° to 150° C. The preferred temperature ranges from 80° to 120° C.

The reaction is advantageously carried out at atmospheric pressure, or under solvent vapor pressure, or under inert gas pressure.

The reaction is generally complete in 2 hours.

However, it is advantageous to continue heating for a period of time of 2 to 8 hours in order to remove any trace amounts of benzoyl chloride. For example, at 95° C. the preferred reaction period ranges from 5 to 7 hours.

The compound containing alkylene oxide recurring units advantageously contains from 2 to 200 units selected from between ethylene oxide and propylene oxide.

It is, for example, a product containing one or more polyoxyethylene chains of the formula:

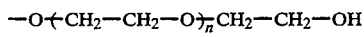

wherein the sum of the n or the n's ranges from 2 to 200.

The ethylene oxide units can be replaced by propylene oxide units, or a mixture of these two units.

Exemplary such polyoxyalkylenated compounds include:
(i) simple polyethylene glycols of the formula:

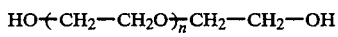

having a molecular weight ranging from 100 to 4,000;
(ii) polyethylene glycols condensed with stearic acid of the formula:

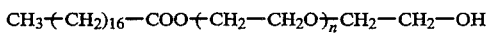

wherein n ranges from 20 to 150;
(iii) triglyceride derivatives of polyethylene glycols;
(iv) polyoxyethylenated alkylphenols of the formula:

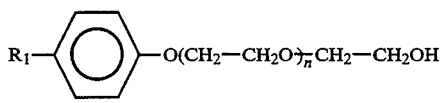

wherein n ranges from 10 to 200 and $R_1$ is an alkyl radical having up to 20 carbon atoms.

Also included are all the polyethylene glycol derivatives which have more than 10 ethylene units.

Products which are similar to the above compounds can also be used, in which the ethylene oxide unit is replaced by the propylene oxide unit or a mixture of ethylene oxide and propylene oxide units.

The amount of this product may range from 0.1 to 10 g per mole of acid halide, with the preferred amount ranging from 0.4 to 2 g.

The product is generally added to the reaction solvent, but it can also be added wholly or partly with the pure of solvent-diluted acid halide.

When the reaction is carried out in a strictly anhydrous medium using carefully dehydrated reactants, the degree of conversion and yield are very low; a very small quantity of a polar compound, such as formamide, glycerol or ethylene glycol, must be added to the reactants to obtain a high yield and degree of conversion.

The polar compound is preferably poorly soluble in the reaction solvent, but must not give rise to the formation of anhydride or acid by reaction with the acid halide.

Compounds whose dielectric constant is higher than 30 are advantageously used, except that water is excluded.

Among the polar compounds which are particularly suitable, the following are representative:
(i) glycerol, $CH_2OH$—$CHOH$—$CH_2OH$;
(ii) ethylene glycol, $CH_2OH$—$CH_2OH$;
(iii) formamide;
(iv) sugar derivatives.

The amount of the polar compound to be added advantageously ranges from 0.1 to 10 g per 1 mole of acid halide.

The preferred amount ranges from 0.25 to 2 g per mole of acid halide.

The manner in which the polar compound is introduced must ensure a good distribution thereof over the reactants.

After the reaction, any excess of cyanide and of alkali metal halide which is formed are removed by filtration. Pure acyl cyanide is obtained by distillation of the filtered reaction mixture.

In order to further illustrate the present invention and the advantages thereof, the following specific examples are given, it being understood that same are intended only as illustrative and in nowise limitative.

In said examples to follow, by "degree of conversion" is intended the amount of acid halide consumed relative to the initial amount thereof and by "yield" is intended the ratio of the number of moles of acyl cyanide produced to the number of moles of acid halide initially present.

Also in said examples to follow, the composition of the filtrate is reported in moles relative to the benzoyl chloride used.

EXAMPLE 1

29.4 g of anhydrous sodium cyanide (0.6 moles) and 0.5 g of glycerol were introduced into a glass reactor fitted with a stirrer and a condenser, containing 150 cm³ of xylene and 0.5 g of polyoxyethylenated nonylphenol marketed by GAF under the trademark Antarox CO 990. These materials were heated to 95° C. under stirring and 70.3 g of benzoyl chloride (0.5 moles) were then introduced over 0.5 hours; the temperature was maintained at 95° C. for 6 hours and then, after cooling, filtration and washing with xylene were carried out. An inorganic precipitate weighing 34.5 g and 241.9 g of filtrate were obtained.

The organic filtrate was analyzed by gas phase chromatography and determined using an internal standard.

| Benzoyl chloride | 0.4% |
| --- | --- |
| Benzoyl cyanide | 93.3% |
| Benzoic anhydride | 0.35% |
| Benzoic acid | 0.0% |
| Dimer | 2.6%. |

This reflects a yield of 93.3% and a degree of the conversion of benzoyl chloride of 99.6%.

EXAMPLE 2

The procedure of Example 1 was repeated, but with the glycerol being replaced with an equal weight of ethylene glycol.

229.1 g of organic filtrate were obtained, containing, in mol % relative to the initial benzoyl chloride:

| Benzoyl chloride | 0.2% |
| --- | --- |
| Benzoyl cyanide | 91.6% |
| Benzoic anhydride | 0.45% |
| Benzoic acid | 0.2% |
| Dimer | 3.1%. |

This reflects a yield of 91.6% and a degree of conversion of 99.8%.

EXAMPLE 3

The procedure of Example 1 was repeated, but with the glycerol being replaced with 1.25 of formamide. After the benzoyl chloride had been introduced over 1 hour, and heating had been continued for 2 hours, an inorganic precipitate of 33.4 g was obtained, and an organic filtrate of 274.5 g, containing:

| Benzoyl chloride | 3.3% |
| --- | --- |
| Benzoyl cyanide | 76.0% |
| Benzoic anhydride | 1.0% |
| Dimer | 10.0%. |

This reflects a yield of 76% and a degree of conversion of 96.7%.

EXAMPLE 4

The procedure of Example 1 was repeated, but with the glycerol being replaced with 0.5 g of glucose. A degree of conversion of 92%, a 73.4% yield and a benzoic anhydride content of 0.65% (molar) in the filtrate were obtained.

EXAMPLE 5

The procedure of Example 1 was repeated, but with the amount of solvent being reduced: 75 cm³ of xylene instead of 150 cm³. 34.4 g of an organic precipitate were obtained and 182.2 g of an organic filtrate containing:

| Benzonitrile | 0.1% |
| --- | --- |
| Benzoyl chloride | 14.8% |
| Benzoyl cyanide | 79.0% |
| Benzoic anhydride | 0.8% |
| Dimer | 3.2%. |

This reflects a yield of 79% and a degree of conversion of 85.2%.

Example 6

Not According to the Invention

The procedure of Example 2 was repeated, but the introduction of the Antarox CO 990 was omitted.

36.6 g of an inorganic precipitate were obtained and 243.4 g of an organic filtrate containing:

| Benzoyl chloride | 57.8% |
| --- | --- |
| Benzoyl cyanide | 39.5% |
| Benzoic acid | 0.2% |
| Benzoic anhydride | 0.8% |
| Dimer | 2.5%. |

This reflects a yield of 39.5% and a degree of conversion of 42.2%.

Example 7

Not According to the Invention

The procedure of Example 1 was repeated, but the addition of polar derivative was omitted.

30.8 g of an inorganic precipitate were obtained and 229 g of an organic filtrate containing (mol %):

| Benzoyl chloride | 68.2% |
| --- | --- |
| Benzoyl cyanide | 23.8% |
| Benzoic acid | 0.3% |
| Benzoic anhydride | 0.5%. |

EXAMPLE 8

The procedure of Example 1 was repeated, but replacing the Antarox CO 990 with the same weight of polyethylene glycol triglyceride containing 150 ethylenated units, marketed by Atlas under the trademark G 1295.

34.9 g of an inorganic precipitate were obtained and an organic filtrate containing, in mol % relative to the initial benzoyl chloride:

| Benzonitrile | 0.2% |
| --- | --- |
| Benzoyl chloride | 1.9% |
| Benzoyl cyanide | 92.3% |
| Benzoic anhydride | 0.45% |
| Dimer | 2.5%. |

This reflects a yield of 92.3% for a degree of conversion of 98.1%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an acyl cyanide having the formula (I):

in which R is an alkyl radical having from 1 to 8 carbon atoms, a cycloalkyl radical having from 3 to 12 carbon atoms, an aryl radical, a heterocyclic radical optionally condensed with a benzene nucleus, or substituted such radicals, comprising reacting in the liquid phase an acid halide of the formula (II):

in which R is as defined above and X is a halogen atom, with an alkali metal cyanide, (a) in an inert anhydrous solvent medium, (b) in the presence of an acyl cyanide yield enhancing amount of a poly(alkylene oxide) compound and (c) in the further presence of a polar compound other than water, wherein the reactants are selected and used in amounts and under conditions which result in the production of said acyl cyanide.

2. The process as defined by claim 1, wherein the amount of alkali metal cyanide ranges from 1 to 2 moles per mole of acid halide.

3. The process as defined by claim 2, said amount of alkali metal cyanide ranging from 1 to 1.25 moles per mole of acid halide.

4. The process as defined by claim 1, said alkali metal cyanide comprising sodium cyanide.

5. The process as defined by claim 1, said solvent medium comprising xylene or toluene.

6. The process as defined by claim 1 wherein the amount of said alkylene oxide compound ranges from 0.1 to 10 g per mole of acid halide.

7. The process as defined by claim 6, said amount of alkylene oxide compound ranging from 0.4 to 2 g per mole of acid halide.

8. The process as defined by claim 1, said polar compound comprising glycerol, ethylene glycol or formamide.

9. The process as defined by claim 1, wherein the amount of said polar compound ranges from 0.1 to 10 g per mole of acid halide.

10. The process as defined by claim 9, said amount of polar compound ranging from 0.25 to 2 g per mole of acid halide.

11. The process as defined by claim 1, said acid halide comprising benzoyl chloride.

12. The process as defined by claim 1, wherein the amount of solvent ranges from 200 to 500 ml per mole of acid halide.

13. A process for the preparation of an acyl cyanide having the formula (I):

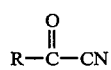

in which R is an alkyl radical having from 1 to 8 carbon atoms, a cycloalkyl radical having from 3 to 12 carbon atoms, an aryl radical, a heterocyclic radical optionally condensed with a benzene nucleus, or substituted such radicals, comprising reacting in the liquid phase an acid halide of the formula (II):

in which R is as defined above and X is a halogen atom, with an alkali metal cyanide, (a) in an inert anhydrous solvent medium, (b) in the presence of an acyl cyanide yield enhancing amount of a poly(alkylene oxide) compound containing 2 to 200 ethylene oxide or propylene oxide recurring units, or combination thereof, and (c) in the further presence of a polar compound other than water, wherein the reactants are selected and used in amounts and under conditions which result in the production of said acyl cyanide.

14. A process for the preparation of an acyl cyanide having the formula (I):

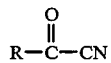

in which R is an alkyl radical having from 1 to 8 carbon atoms, a cycloalkyl radical having from 3 to 12 carbon atoms, an aryl radical, a heterocyclic radical optionally condensed with a benzene nucleus, or substituted such radicals, comprising reacting in the liquid phase an acid halide of the formula (II):

in which R is as defined above and X is a halogen atom, with an alkali metal cyanide, (a) in an inert anhydrous solvent medium, (b) in the presence of an acyl cyanide yield enhancing amount of a poly(alkylene oxide) compound containing one or more of the chains: —O—(CH$_2$—CH$_2$—O)$_n$—CH$_2$—CH$_2$—OH where n ranges from 2 to 200, and (c) in the further presence of a polar compound other than water, wherein the reactants are selected and used in amounts and under conditions which result in the production of said acyl cyanide.

15. The process as defined by claim 1, wherein said anhydrous solvent medium (a) is not said alkylene oxide compound (b).

* * * * *